United States Patent [19]

Kawai et al.

[11] Patent Number: 4,687,764

[45] Date of Patent: Aug. 18, 1987

[54] HYPOTRIGLYCERIDEMICALLY ACTIVE POLYSACCHARIDES

[75] Inventors: Yasuo Kawai, Atsugi; Kazunaga Yazawa, Sagamihara, both of Japan

[73] Assignee: Kabushiki Kaisha Advance Kaihatsu Kenkyujo, Tokyo, Japan

[21] Appl. No.: 632,844

[22] Filed: Jul. 20, 1984

[30] Foreign Application Priority Data

Jul. 27, 1983 [JP] Japan ................. 58-135982

[51] Int. Cl.$^4$ .................. A61K 31/71; C07H 1/00
[52] U.S. Cl. ..................... 514/54; 536/1.1; 435/75
[58] Field of Search ............. 536/1.1; 514/54

[56] References Cited

U.S. PATENT DOCUMENTS 4,357,323  11/1982  Soma et al. ............... 514/54
4,536,496  8/1985   Shimizu et al. ........... 514/54

OTHER PUBLICATIONS

Kawai, *The American Journal of Clinical Nutrition*, 32: Jan. 1979, pp. 187–188.
Kawai et al, *Mechanisms of Ageing and Development*, 16 (1981), 149–158.
Yazawa et al, *Mechanism of Ageing and Development*, 17 (1981), 173–182.
Watanabe et al., *Microbiol. Immunol.*, vol. 25(3), 257–269, 1981.
Kawai et al., *Microbiol. Immunol.*, vol. 26(5), 363–373, 1982.
Kawai et al, *The American Journal of Clinical Nutrition*, 33: Nov. 1980, pp. 2458–2461.
Kawai et al, *Infection and Immunity*, vol. 19, No. 3, Mar. 1978, pp. 771–778.

*Primary Examiner*—Johnnie R. Brown
*Assistant Examiner*—Elli Peselev
*Attorney, Agent, or Firm*—Finnegan, Henderson, Farabow, Garrett & Dunner

[57] ABSTRACT

A hypotriglyceridemically active polysaccharide having the following characteristics:
(a) Specific rotatory power:
  $[\alpha]_D^{29} = +190.1$
  (1.8 w/v % solution)
(b) Molecular weight by gel filtration:
  $14,000 \pm 3,000$
(c) Sugar composition (weight percent by gas chromatography)
  glucose: 70.3
  rhamnose: 13.7
  uronic acid: 16.0
(d) Acid-base characteristic:
  neutral polysaccharides
(e) Physiological characteristics:
  capable of reducing the blood triglyceride in mammals.

This hypotriglyceridemically active polysaccharide can be prepared by cultivating a microorganism belonging to the genus Streptococcus in an adequate culture medium therefor; and collecting the hypotriglyceridemically active polysaccharide from the cultured cells of the microorganism and/or the supernatant of the culture broth. The present hypotriglyceridemically active polysaccharide can be used as an active ingredient of a hypotriglyceridemic or antiatherosclerotic pharmaceutical composition together with a pharmaceutically acceptable carrier therefor to form a hypotriglyceridemic or antiatherosclerotic pharmaceutical composition, which is suitable for oral administration to mammals.

12 Claims, 4 Drawing Figures

4,687,764

HYPOTRIGLYCERIDEMICALLY ACTIVE POLYSACCHARIDES

BACKGROUND OF THE INVENTION

1. Field of the Invention

The present invention relates to a novel hypotriglyceridemically active polysaccharide (i.e., triglyceride-reducing polysaccharide, "TRS"), a process for preparing the same, a hypotriglyceridemically active and/or antiatherosclerotic pharmaceutical composition containing the same, and a method for reducing blood triglyceride in mammals.

2. Description of the Prior Art

As is well-known in the art, several pharmaceutical preparations such as clofibrate and its related preparations have been proposed as therapeutical medicines for atherosclerosis or hyperlipidemia, considered to be a typical middle-aged or geriatric disease. However, the desired purposes are not fully satisfied by these known medicines from the viewpoint of, for example, pharmacological effects and side-effects, and there is a strong demand for the development of safe and more effective medicines.

SUMMARY OF THE INVENTION

Accordingly, an object of the present invention is to provide a novel hypotriglyceridemically active polysaccharide, TRS, which can be safely administered to mammals.

Another object of the present invention is to provide a process for preparing a novel triglyceridemically active polysaccharide capable of effectively reducing the blood triglyceride in mammals.

A further object of the present invention is to provide a hypotriglyceridemic or antiatherosclerotic pharmaceutical composition containing, as an active ingredient, a novel polysaccharide, TRS.

A still further object of the present invention is to provide a method for reducing the blood triglyceride in mammals.

Other objects and advantages of the present invention will be apparent from the description set forth hereinbelow.

In accordance with the present invention, there is provided a hypotriglyceridemically active polysaccharide having the following characteristics:

(a) Specific rotatory power: $[\alpha]_D^{29} = +190.1$ (1.8 w/v% solution)

(b) Molecular weight by gel filtration: $14,000 \pm 3,000$ (c) Sugar composition (weight percent by gas chromatography):
glucose: 70.3
rhamnose: 13.7
uronic acid: 16.0

(d) Acid-base characteristic: neutral polysaccharides (e) Physiological characteristics: capable of reducing the blood triglyceride in mammals.

This hypotriglyceridemically active polysaccharide can be prepared by cultivating a microorganism belonging to the genus Streptococus in an adequate culture medium therefor; and collecting the hypotriglyceridemically active polysaccharide from the cultured cells of the microorganism and/or the supernatant of the culture broth. The present hypotriglyceridemically active polysaccharide can be used as an active ingredient of a hypotriglyceridemic or antiatherosclerotic pharmaceutical composition together with a pharmaceutically acceptable carrier therefor, to form a hypotriglyceridemic or antiatherosclerotic pharmaceutical composition, which is suitable for oral administration to mammals.

BRIEF DESCRIPTION OF THE DRAWING

The present invention will be better understood from the description set forth below with reference to the accompanying drawings, in which.

DESCRIPTION OF THE PREFERRED EMBODIMENTS

Figure 1:
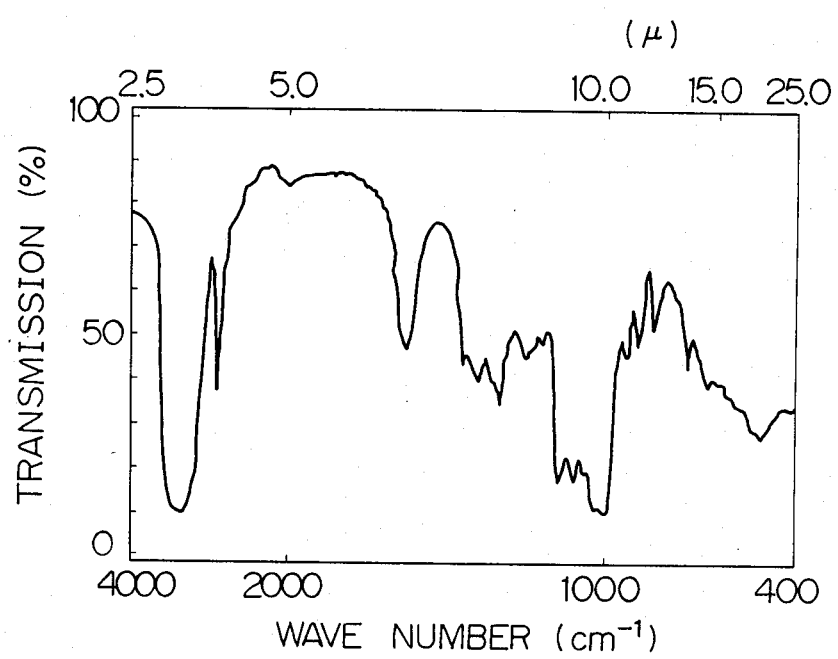
FIG. 1 illustrates an infrared absorption spectrum profile of the TRS polysaccharide of the present invention.

The present inventors found that the novel polysaccharides obtained from microorganisms belonging to the genus Streptococcus and/or the supernatant of culture broth can effectively reduce the blood triglyceride, and that this constituent extracted from these so-called gastrointestinal bacteria and the supernatant of culture broth is substantially nontoxic when orally administered.

The microorganisms used in the preparation of the product, the manufacturing methods, the physicochemical characteristics, and the pharmacological effects of the TRS polysaccharide according to the present invention will now be shown in detail hereinbelow.

MIROORGANISMS

1. Species

Microorganisms utilizable in the present invention belonging to the genus Streptococcus: *Streptococcus faecium*, *Streptococcus faecalis*, *Streptococcus bovis*, *Streptococcus avium*, *Streptococcus durans*, *Streptococcus salivarius*, *Streptococcus mitis*, *Streptococcus equinus*, and others are preferably shown.

Typical examples of such microorganisms were deposited in the Fermentation Research Institute (FRI, i.e., International Depository Authority under Budapest Treaty) in Japan and the deposition numbers are listed below in Table 1.

TABLE 1

| Strains | Desposition number |
| --- | --- |
| Streptococcus faecium | FERM BP-296 |
| Streptococcus faecalis | FERM BP-297 |
| Streptococcus avium | FERM BP-298 |
| Streptococcus salivarius | FERM BP-299 |
| Streptococcus durans | FERM BP-300 |
| Streptococcus mitis | FERM BP-301 |
| Streptococcus equinus | FERM BP-302 |

2. Microbiological characteristics of microorganisms

General microbiological characteristics

The microbiological characteristics of the microorganisms in the present invention are the same as those of known microorganisms belonging to the identical class. That is, the general microbiological characteristics, cultivation methods and other properties correspond to those described in the following articles:

(1) Bergey's Manual of Determinative Bacteriology, 8th, ed., 490–509 (1974).

(2) Int. J. Syst. Bact. 16, 114 (1966).

(3) Microbiol. Immunol. 25 (3), 257–269 (1981).

(4) J. Clin. Pathol. 33, 53–57 (1980).
(5) J. General Microbiol. 128, 713–720 (1982).
(6) Applied Microbiol. 23 (6), 1131–1139 (1972).

The typical microbiological properties of the above-exemplified strains according to the present invention are summarized as shown in Table 2.

TABLE 2

| Characteristics | Strains FERM BP | | | | | | |
|---|---|---|---|---|---|---|---|
| | -296 | -297 | -298 | -299 | -300 | -301 | -302 |
| Shape of cell | spheroid | | | | | | |
| Gram stain | + | + | + | + | + | + | + |
| Hemolysis | α | α | α | α | α | α | α |
| Growth at 10° C. | + | + | ± | − | + | − | − |
| Growth at 45° C. | + | + | + | ± | + | ± | + |
| Growth at 50° C. | + | − | − | − | + | − | − |
| Thermal resistance at 60° C. for 30 min | + | + | + | − | + | − | − |
| Growth in culture medium at pH 9.6 | + | + | + | − | + | − | − |
| Methylene blue reduction ability | + | + | − | − | + | − | − |
| Liquefaction of gelatin | − | − | − | − | − | − | − |
| Growth in culture medium containing NaCl (6.5%) | + | + | − | − | + | − | − |
| Growth in culture medium containing bile (40%) | + | + | + | − | + | − | + |
| Productivity of ammonia | + | + | ND*2 | − | + | ± | − |
| Hydrolysis of hippuric acid | − | ± | − | − | + | − | − |
| Growth in culture medium containing tellurite | − | + | − | ND | − | ND | − |
| Growth in culture medium containing TTC*1 | − | + | − | ND | − | ND | − |
| Acid production from carbon source | | | | | | | |
| Glucose | + | + | + | + | + | + | + |
| Esculin | ± | + | + | + | ± | ND | + |
| Inulin | − | − | − | + | − | − | ± |
| Lactose | + | + | + | ± | + | ± | − |
| Glycerol | − | + | ± | − | − | − | − |
| Arabinose | + | − | + | − | − | − | − |
| Melezitose | − | + | ± | ND | − | ND | − |
| Sorbitol | − | + | + | − | − | − | − |
| Antigenic group | D | D | Q(D) | K | D | − | D |

*1 2,3,5-triphenyltetrazolium chloride
*2 Not done

3. Cultivating methods

These microorganisms can be cultivated in a conventional manner. For example, the bacterial cells can be collected by stationary cultivation in a Rogosa broth medium having the following composition under an aerobic condition, and can be harvested by centrifugation of the culture.

| Composition of Rogosa broth medium | |
|---|---|
| Trypticase | 10 g |
| Yeast extract | 5 g |
| Tryptose | 3 g |
| K$_2$HPO$_4$ | 3 g |
| KH$_2$PO$_4$ | 3 g |
| Triammonium citrate | 2 g |
| Tween 80 | 1 g |
| Glucose | 20 g |
| Cysteine hydrochloride | 0.2 g |
| Salt solution*1 | 5 ml |
| Distilled water | to 1 liter |
| (pH 7, heat sterillization at 121° C. for 15 minutes) | |

*1 MgSO$_4$.7H$_2$O  11.5 g
FeSO$_4$.7H$_2$O  0.68 g
MnSO$_4$.2H$_2$O  2.4 g
Distilled water  100 ml

Preparation of the TRS polysaccharide

An example of typical procedures for preparation of the TRS polysaccharide according to the present invention is given as follows:

1. Collection of microorganisms

Each of the microbial strains shown above is inoculated into a Rogosa broth medium and incubated without agitation at 37° C. for 5 to 10 hours under an aerobic condition, to yield a subsequent culture broth at a certain viable bacterial cell concentration. The culture broth is continuously centrifuged at 12,000 rpm, and the harvested bacterial cells are then washed in saline (0.85% NaCl) 2 to 3 times.

2. Disruption of bacterial cells (a) The washed cells are suspended in physiological saline and heat-treated at 115° C. for 10 min to be disrupted.

(b) The bacterial cells washed and suspended in physiological saline are disrupted by sonication (15 KC, 60 min), French press, and other conventional methods.

3. Removal of fat from the cell

The disrupted cell suspension is mixed with chloroform-methanol (2:1, v/v). The components extractable by the organic solvent are then completely removed by centrifugation at 3,000 rpm for 10 min and the chloroform layer is discarded.

4. Treatment with proteolytic enzymes

The defatted sample mentioned above is treated with proteolytic enzymes such as pronase, trypsin, and pepsin under ordinary procedures. Of these proteolytic enzymes, pronase is most useful for the purpose. The conditions of the treatment with this enzyme are referred to in "Methods in Enzymology", Vol. VIII, p. 26 (1966).

5. Purification

The centrifugal supernatant of the proteolytic reaction mixture is added with precipitants such as trichloroacetic acid or ammonium sulfate to precipitate and to remove the protein fraction. The supernatant fraction is then treated with appropriate nucleases or proteolytic enzymes to remove nucleic acid constituents such as DNA and RNA or proteins in the fraction. Dialysis is repeatedly made after such enzymatic treatments.

The partly purified fraction is then subjected to the repetition of further purification procedures such as gel filtration and column chromatography, and finally, a pure preparation of polysaccharide designated as the TRS polysaccharide is obtained.

In general, this TRS polysaccharide can be prepared according to its physicochemical characteristics, mentioned below, by many of the isolation and purification procedures already widely employed in the field concerned, such as precipitation-dissolution and extraction, solvent extraction, dialysis, column chromatography, electrophoresis, gel filtration, or any combination of these procedures. Therefore, the present invention is by no means limited to a specified procedure.

That is, the preparation of the present invention is related to the preparation methods of hypotriglyceridemically active products, which are composed of polysaccharide and obtained from microorganisms belonging to the genus Streptococcus, because the pharmacological activity is found in the polysaccharide fraction. This is described in detail in each example hereinbelow.

Note, the hypotriglyceridemic activity in the supernatant of the culture broth is about 1/5 of that in the bacterial cell.

Physicochemical characteristic of the TRS polysaccharide

The physicochemical and physiological characteristics of the TRS polysaccharide of the present invention are as follows.

1. Chemical nature and solubilizing properties

The powdered sample obtained after desalting and freeze-drying was a non-deliquescent white powder and was highly soluble ($\sim 100$ mg/ml) in water, but only partly soluble in ethanol, methanol, and acetone, and insoluble in ether and chloroform.

2. Molecular weight

The molecular weight of the TRS polysaccharide was estimated at 14,000±3,000 by gel filtration, with several dextrans of different molecular weight as indices, using a Toyopearl HW 55 column (Toyosoda Co., Ltd.) equilibrated with a 25 mM tris-HCl buffer containing 0.3M NaCl (pH 7.5).

3. Specific rotatory power

The specific rotatory power of the said TRS polysaccharide in 1.8 w/v% solution, $[\alpha]_D^{29}$, is +190.1 (dextro-rotation), as determined by a polarimeter (model DIP-4, Japan Spectroscopic Co., Ltd.).

4. Sugar composition (a) Four mg of the sample was treated with 0.2M TFA (trifluoroacetic acid) at 100° C. for 7 hrs, and trimethylsilylated as follows; the sample was mixed with 0.2 ml hexamethyldisilazane (20% v/v in pyridine) and 0.02 ml trimethylchlorosilane, agitated for 15 min, and, after standing for 5 min, subjected to gas chromatography to determine glucose, rhamnose, etc. The separation column temperature was 179° C. Uronic acid, etc. were determined by a carbazole-$H_2SO_4$ method (modified Bitter-Muir method; Bitter, T. and Muir, H. Anal. Biochem. 4, 330 (1962)). The sugar composition of the TRS polysaccharide was glucose 70.3%, rhamnose 13.7%, and uronic acid 16.0%.

5. Acid-base characteristic

The pH of the 0.1 and 0.5% solution of the TRS polysaccharide was 6.71.

6. Infrared absorption spectrum

The infrared absorption spectrum of the TRS polysaccharide, measured by an infrared spectrometer (model JASCO A-302, Japan Spectroscopic Co., Ltd.) is shown in FIG. 1, in which the abscissa and ordinate show the wave number and percent transmission, respectively.

7. Elementary analysis

An elementary analysis by an element analyzer (model 240 B, Perkin-Elmer) showed a result of C 37.2%, H 6.4%, and O 56.4% of the TRS polysaccharide. The rational formula is $C_{31}H_{64}O_{35}$.

8. Melting point

The melting point of the TRS polysaccharide was 235°~241° C., measured with a melting point apparatus (model Yanaco MP-3, Yanagimoto Seisakusho, Japan).

9. Physiological characteristics

The TRS polysaccharide is active in reducing the blood triglyceride level in mammals when administered orally.

This activity is stable within the range of at least −80° C. to 115° C. and at pH 4.1 to 11, when the TRS polysaccharide is stored.

Pharmacological actions of the TRS polysaccharide

1. Pharmacological effects

As shown in each example hereinbelow, the present antiatherosclerotic drug composed of the TRS polysaccharide of the present invention is extremely effective in reducing the blood triglyceride level in mammals. Accordingly, this drug is useful as a therapeutic or preventive medicine for diseases closely related to atherosclerosis, hyperlipidemia, hyperlipoproteinemia, xanthomatosis, cholecystolithiasis, hypertension, diabetes, and others.

The preparation of the present invention can be administered to mammals via oral, intraperitoneal, and intravenous, and other administration routes. The amount per dosage is about 1 μg to 0.5 g/kg body weight. The oral administration of about 0.01 mg to 100 mg/kg body weight is preferred. Any drug form of the present invention can be chosen and used as a solution in physiological saline and others, injections, powder made by lyophilization, etc., suppository, enteric-coated tablets, sublingual tablets, granules, tablets, capsules, etc. with appropriate carriers, diluent bases, diluents, etc.

2. Acute toxicity

As shown in the examples hereinbelow, an $LD_{50}$ of the TRS polysaccharide according to the present invention is more than 1,200 mg/kg body weight, administered intraperitoneally to mice. The substance is substantially nontoxic on oral administration.

EXAMPLES

The present invention will now be further shown by, but is by no means limited to, the following examples.

EXAMPLE 1

Preparation and purification of the TRS polysaccharide

Streptococcus faecium FERM BP-296 was inoculated into 2 l of Rogosa broth medium at a final concentration of $1 \times 10^6$ bacteria/ml. The inoculated medium was incubated at 37° C. for 10 hrs without agitation under an aerobic condition to yield $10^9$ bacteria/ml of culture broth. The bacterial cells were harvested by continuous centrifugation at 12,000 rpm, washed with physiological saline (0.85% NaCl), and suspended in the same solution to obtain 100 ml of the cell suspension at a concentration of $2 \times 10^{10}$/ml.

The above bacterial cell suspension was heat-treated at 115° C. for 10 minutes and treated 3 times with chloroform-methanol (2:1, v/v) to remove fats.

The defatted bacterial suspension was centrifuged at 3,000 rpm for 10 minutes and the lower layer, i.e., the chloroform layer, was discarded. The aqueous layer was employed as a starting material in the following purification steps.

The starting material was then treated with 20 mg pronase (Sigma protease type XIV) in 100 ml of phosphate buffer (pH 7.8) containing 0.0015M $CaCl_2$ at 47° C. for 24 hrs, and further treatment with 10 mg of pronase was carried out under the same conditions. The experimental conditions of the treatment with pronase are referred to in 'Methods in Enzymology', Vol. VIII, p. 26 (1966).

The material treated with pronase was divided into the precipitation and supernatant fractions by centrifugation at 3,000 rpm for 10 minutes. The supernatant fraction was added with 1/9 volume of 100% (w/v) trichloroacetic acid (TCA), stood at 4° C. for 3 hrs with agitation, and then centrifuged at 3,000 rpm for 10 minutes to obtain the precipitation and supernatant fractions. The precipitation fraction was added with the same volume of 10% TCA and the same process was repeated. The obtained supernatant was washed 3 times with ethyl ether to remove TCA, dissolved in 50 ml of distilled water, neutralized with 1N NaOH, dialyzed to remove TCA completely, and finally lyophilized to yield 258 mg (dry weight) of the supernatant fraction.

The obtained supernatant fraction was treated with the pronase described above, and dialyzed to yield 176 mg (dry weight) of the dialyzed fraction (MW>3,500). The dialyzed fraction was designated as Purified fraction I.

Figure 2:
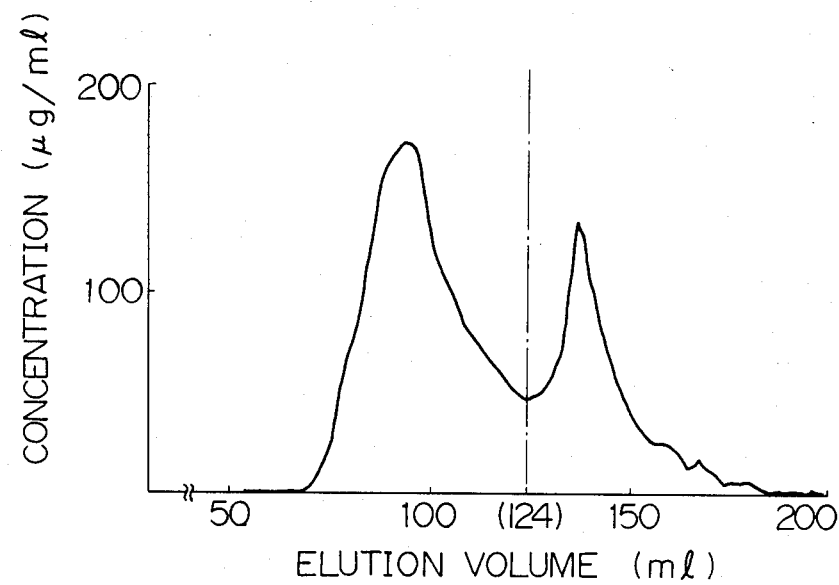
FIGS. 2 to 4 illustrate the elution patterns of gel filtration in Example 1 set forth hereinafter.

The above Purified fraction I was fractionated by Sephadex G-100 (Pharmacia) column chromatograph equilibrated with 0.05M Tris-HCl buffer. The column chromatogram of the Purified fraction I at an elution rate of 1 ml/min is shown in FIG. 2; the abscissa shows the elution volume (ml), and the ordinate shows the concentration of eluted substance (μg/ml). A fraction after 124 ml was collected and designated as Purified fraction II (93.6 mg dry weight).

Figure 3:
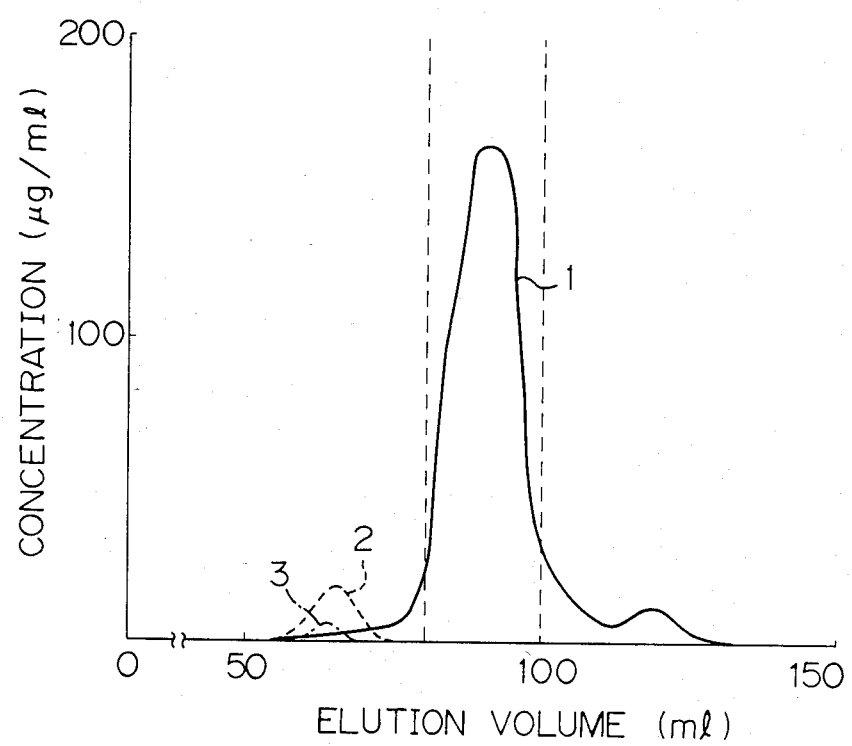

FIG. 3 shows a column chromatogram of the purified fraction II determined by a Toyopearl HW-55F column equilibrated with a 25 mM Tris-HCl buffer containing 0.3M NaCl. The elution rate was 1 ml/min. In FIG. 3, lines 1, 2, and 3 show the elution profiles of sugar, protein, and nucleic acid, respectively.

The purified TRS polysaccharide (87.9 mg dry weight) was isolated by collecting the portion eluted in 80~100 ml fractions.

Figure 4:
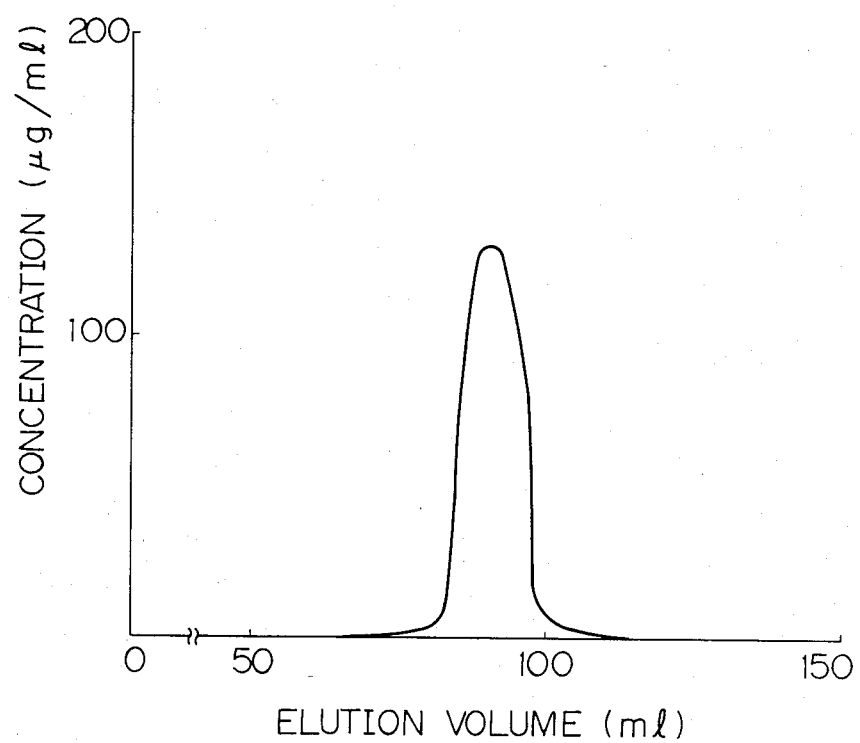

FIG. 4 shows the column chromatogram of TRS polysaccharide under the same experimental conditions as shown in FIG. 3.

The physicochemical characteristics of the TRS polysaccharide were as shown above.

Table 3 shows the yield and the amounts of protein determined by the Lowry method, RNA by the orcinol method, DNA by the diphenylamine method, and sugar by the phenol-$H_2SO_4$ method in each preparation process. The values in the table indicate the dry weight (mg) of the yield and the weight % of the chemical components.

TABLE 3

| Fractions | Yield | Protein | RNA | DNA | Sugar | Specific activity |
|---|---|---|---|---|---|---|
| Supernatant | 258 | 14.1 | 1.8 | trace | 76.3 | 7.1 |
| Purified fraction I | 176 | 2.8 | 1.6 | trace | 95.6 | 10.2 |
| Purified fraction II | 93.6 | 2.1 | 0.9 | trace | 97.0 | 12.3 |
| TRS polysaccharide | 87.9 | trace | trace | trace | 100 | 23.0 |

The specific activity shown in Table 3 indicates the relative activity of triglyceride reduction by each fraction in conventional rats per unit weight where that of the heat-treated bacterial cells mentioned above is 1. Assay methods for triglyceride-reducing activity in animal experiments are shown below in Example 2.

It was confirmed that the TRS polysaccharide can be separated and purified from other bacterial strains listed in Table 1, as well as in this example, but with little variety in the yield.

EXAMPLE 2

Pharmacological effect of the TRS polysaccharide

1. Hypotriglyceridemic activity (1)

Physiological saline samples containing the equivalent of 16 mg/kg body weight of the lyophilized TRS polysaccharide were prepared. These samples were orally administered at a daily dosage of 1 ml to conventional rats (18 week-old, male, average body weight 246 g, 10 rats per group) and conventional and germfree mice (18 week-old, male, average body weight 30 g, 10 mice per group). The rats and mice were bred for 8 to 12 weeks. Arterial blood was then collected from the abdominal aorta of these animals and serum samples were separated by centrifugation from the whole blood. The triglyceride level was determined by using Triglyceride TG WAKO (Wako Junyake Co., Ltd., Acetyl acetone method).

The results are summarized in Table 4. The values listed in the table are reduction rate (%) from the values in the control groups to which no sample is dosed. The composition (% by weight) of the diet, given ad libitum, is shown in Table 5.

TABLE 4

| Animals | Reduction rate (%) |
|---|---|
| Conventional rats (12 weeks) | 40.5 |
| Conventional mice (8 weeks) | 45.1 |
| Germfree mice (8 weeks) | 39.6 |

TABLE 5

| Composition | Weight % |
|---|---|
| Casein | 20 |
| Soybean oil | 10 |
| Wheat starch | 61 |
| Minerals | 4 |
| Vitamin mixture | 2 |
| Powdered filter paper | 3 |

2. Hypotriglyceridemic activity (2)

The above-mentioned samples were orally administered at a daily dosage of 1 ml to conventional rats (18 week-old, male, average body weight 238 g, 15 rats per group) and conventional and germfree mice (18 week-old, male, average body weight 31 g, 10 mice per group) for 4 weeks. The blood triglyceride level was determined as mentioned above. The results are shown in Table 6.

The terms cholesterol-loaded and fructose-loaded in the table mean the addition of 1% cholesterol into the above-mentioned diet and the substitution of fructose for the total amount of wheat starch in the above-mentioned diet, respectively. The values in the table are the reduction rate (%) from the values of the no dosage control group.

TABLE 6

| Animals | Reduction rate (%) |
|---|---|
| Germfree mice[*1] | 45.4 |
| Conventional mice[*1] | 41.6 |
| Conventional rats[*1] | 43.2 |
| Conventional rats[*2] | 42.0 |

[*1]Cholesterol-loaded diet
[*2]Fructose-loaded diet

3. Hypotriglyceridemic activity (3)

Physiological saline samples containing 4 mg/ml of the TRS polysaccharide were orally administered at a daily dosage of 1 ml per rat for 2 weeks to hyperlipidemic rats (18 week-old, male, average body weight 250 g, 5 rats per group) fed with a cholesterol-loaded diet. The blood triglyceride level was determined as mentioned above. The results are shown in Table 7. The value of the administration group is the triglyceride reduction rate (%) to the no dosage control group.

TABLE 7

| Animals | Reduction rate (%) |
|---|---|
| Administered | 45.0 |
| Control | 0 |

4. Dose response

Physiological saline samples containing 0.1 mg~20 mg/ml of the TRS polysaccharide were orally administered at a daily dosage of 1 ml per to conventional rats (6 week-old, male, average body weight 216 g, 5 rats per group) for 4 weeks. The blood triglyceride level was determined as mentioned above (control group was no dosed group). The results are shown in Table 8.

TABLE 8

| Dosage (mg/rat) | Reduction rate (average %) |
|---|---|
| Control | 0 |
| 0.1 | <10.0 |
| 1 | 17.4 |
| 10 | 43.0 |
| 20 | 48.2 |

5. Acute toxicity

Physiological saline samples (0.5 ml/mouse) containing 1, 10, and 100 mg of the TRS polysaccharide were intraperitoneally administered to ICR mice (6 week-old male, average body weight 31.6±0.6 g, 10 mice per group). The thanatobiologic observation of mice was carried out for 14 days. The control material was physiological saline.

The LD50 value calculated according to the Behrens-Kärber method was more than 1,200 mg/kg body weight. The substance was substantially nontoxic on oral administration.

6. Pharmaceutical preparations (1) A 25 mg amount of the purified TRS polysaccharide was uniformly mixed with 275 mg of purified starch powder, and the tablets for oral administration were then formed. Each tablet corresponds to a dosage of $10^{10}$ heat-treated cells/kg body weight for an adult having a body weight of 50 kg.

(2) The TRS polysaccharide is uniformly mixed with diluent bases such as calcium carbonate, lactose, etc., lubricants such as stearic acid, talcum, etc., and other additives, and the tablets then can be formed for oral administration. The daily dosage of the TRS polysaccharide is usually 0.1 mg~100 mg/kg body weight.

(3) The TRS polysaccharide (900 mg) was suspended and dissolved in distilled water (30 ml) sweetened with syrup, and syrups were then formed.

We claim:

1. A polysaccharide having the following characteristics:
   (a) Specific rotatory power:
      $[\alpha]_D^{29} = +190.1$
      (1.8 w/v% solution)
   (b) Molecular weight by gel filtration:
      14,000±3,000
   (c) Sugar composition (weight percent by gas chromatography:
      glucose: 70.3
      rhamnose: 13.7
      uronic acid: 16.0
   (d) Acid-base characteristics:
      neutral polysaccharides
   (e) Physiological characteristics:
      capable of reducing the blood triglyceride in mammals.

2. A polysaccharide as claimed in claim 1, wherein the hypotriglyceridemically active polysaccharide is derived from a microorganism belonging to the genus Streptococcus.

3. A polysaccharide as claimed in claim 2, wherein said microorganism is at least one member selected from the group consisting of S. faecium, S. faecalis, S. avium, S. bovis, S. salivarius, S. durans, S. mitis, and S. equinus.

4. A polysaccharide as claimed in claim 2, wherein said microorganism is at least one member selected from the group consisting of S. faecium FERM BP-296, S. faecalis FERM BP-297, S. avium FERM BP-298, S. salivarius FERM BP-299, S. durans FERM BP-300, S. mitis FERM BP-301, and S. equinus FERM BP-302.

5. A pharmaceutical composition comprising (A) a preventively or therapeutically effective amount of a hypotriglyceridemically active polysaccharide capable of reducing the blood triglyceride in mammals having the following characteristics:
   (a) Specific rotatory power:
      $[\alpha]_D^{29} = +190.1$
      (1.8 w/v% solution)
   (b) Molecular weight by gel filtration:
      14,000±3,000
   (c) Sugar composition (weight percent by gas chromatography)
      glucose: 70.3
      rhamnose: 13.7
      uronic acid: 16.0
   (d) Acid-base characteristics:
      neutral polysaccharides, and (B) a pharmaceutically acceptable carrier therefor.

6. A pharmaceutical composition as claimed in claim 5, wherein said hypotriglyceridemically active polysaccharide is derived from a microoganism belonging to the genus Streptococcus.

7. A pharmaceutical composition as claimed in claim 6, wherein said microorganism is at least one member selected from the group consisting of *S. faecium, S. faecalis, S. avium, S. bovis, S. salivarius, S. durans, S. mitis,* and *S. equinus.*

8. A pharmaceutical composition as claimed in claim 6, wherein said microorganism is at least one strain selected from the group consisting of *S. faecium* FERM BP-296, *S. faecalis* FERM BP-297, *S. avium* FERM BP-298, *S. salivarius* FERM BP-299, *S. durans* FERM BP-300, *S. mitis* FERM BP-301, and *S. equinus* FERM BP-302.

9. A method for reducing the blood triglyceride in mammals comprising *orally* administering to the mammals an effective amount of a hypotriglyceridemically active polysaccharide capable of reducing the blood triglyceride in mammals having the following characteristics:

(a) Specific rotatory power:
$[\alpha]_D^{29} = +190.1$
(1.8 w/v% solution)

(b) Molecular weight by gel filtration:
$14,000 \pm 3,000$ (c) Sugar composition (weight percent by gas chromatography)
glucose: 70.3
rhamnose: 13.7
uronic acid: 16.0

(d) Acid-base characteristics:
neutral polysaccharides.

10. A method as claimed in claim 9, wherein said hypotriglyceridemically active polysaccharide is derived from a microorganism belonging to the genus Streptococcus.

11. A method as claimed in claim 10, wherein said microorganism is at least one member selected from the group consisting of *S. faecium, S. faecalis, S. avium, S. bovis, S. salivarius, S. durans, S. mitis,* and *S. equinus.*

12. A method as claimed in claim 10, wherein said microorganism is at least one strain selected from the group consisting of *S. faecium* FERM BP-296, *S. faecalis* FERM BP-297, *S. avium* FERM BP-298, *S. salivarius* FERM BP-299, *S. durans* FERM BP-300, *S. mitis* FERM BP-301, and *S. equinus* FERM BP-302.

* * * * *